(12) United States Patent
Yu et al.

(10) Patent No.: US 11,571,490 B2
(45) Date of Patent: Feb. 7, 2023

(54) ANTI-MICROBIAL ARTICLES AND METHODS OF USING SAME

(71) Applicant: 3M INNOVATIVE PROPERTIES COMPANY, St. Paul, MN (US)

(72) Inventors: Ta-Hua Yu, Woodbury, MN (US); Junkang Jacob Liu, Woodbury, MN (US); Narina Y. Stepanova, Inver Grove Heights, MN (US); Badri Veeraraghavan, Woodbury, MN (US); Moses M. David, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 313 days.

(21) Appl. No.: 15/568,719

(22) PCT Filed: Jun. 29, 2016

(86) PCT No.: PCT/US2016/040136
§ 371 (c)(1),
(2) Date: Oct. 23, 2017

(87) PCT Pub. No.: WO2017/004231
PCT Pub. Date: Jan. 5, 2017

(65) Prior Publication Data
US 2018/0154037 A1 Jun. 7, 2018

Related U.S. Application Data

(60) Provisional application No. 62/185,887, filed on Jun. 29, 2015.

(51) Int. Cl.
*A61L 15/44* (2006.01)
*A61L 15/18* (2006.01)
(Continued)

(52) U.S. Cl.
CPC ........ *A61L 15/44* (2013.01); *A61F 13/00029* (2013.01); *A61F 13/00063* (2013.01);
(Continued)

(58) Field of Classification Search
CPC ........... A61F 2013/51047; A61L 15/46; A61L 27/50; C08J 7/04; C08J 7/044; C08K 3/22; B82Y 30/00; B82Y 40/00
(Continued)

(56) References Cited

U.S. PATENT DOCUMENTS

| | | | |
|---|---|---|---|
| 3,389,827 A | 6/1968 | Abere | |
| 3,645,835 A | 2/1972 | Hodgson | |

(Continued)

FOREIGN PATENT DOCUMENTS

| | | | |
|---|---|---|---|
| JP | 2011/183567 A | 9/2011 | |
| JP | 2012/250527 A | 12/2012 | |

(Continued)

OTHER PUBLICATIONS

Marino, "Electrical Augmentation of the Antimicrobial Activity of Silver-Nylon Fabrics", Journal of Biological Physics, 1984, vol. 12, No. 4, pp. 93-98.

(Continued)

*Primary Examiner* — Caitlin A Carreiro
(74) *Attorney, Agent, or Firm* — 3M Innovative Properties Company

(57) ABSTRACT

An article having anti-microbial effect is provided. The article includes an occlusive layer and a substrate having a nanostructured surface. The nanostructured surface is coated with a metal oxide layer and the metal oxide layer includes a metal oxide.

12 Claims, 1 Drawing Sheet

(51) Int. Cl.
  *A61L 15/46* (2006.01)
  *A61F 13/00* (2006.01)
  *A61L 15/24* (2006.01)

(52) U.S. Cl.
  CPC ........ *A61F 13/00068* (2013.01); *A61L 15/18* (2013.01); *A61L 15/24* (2013.01); *A61L 15/46* (2013.01); *A61L 2300/102* (2013.01); *A61L 2300/104* (2013.01); *A61L 2300/404* (2013.01); *A61L 2400/12* (2013.01); *A61L 2420/02* (2013.01)

(58) Field of Classification Search
  USPC .............. 602/43, 42, 48; 604/301, 360, 367; 424/445, 447; 216/11; 428/141, 148
  See application file for complete search history.

(56) References Cited

U.S. PATENT DOCUMENTS

| | | |
|---|---|---|
| 4,112,213 A | 9/1978 | Waldman |
| 4,310,509 A | 1/1982 | Berglund |
| 4,323,557 A | 4/1982 | Rosso |
| 4,364,995 A | 12/1982 | Crawford |
| 4,472,480 A | 9/1984 | Olson |
| 4,476,590 A | 10/1984 | Scales |
| 4,595,001 A | 6/1986 | Potter |
| 4,737,410 A | 4/1988 | Kantner |
| 4,982,742 A | 1/1991 | Claude |
| 5,088,483 A | 2/1992 | Heinecke |
| 5,160,315 A | 11/1992 | Heinecke |
| 5,454,886 A | 10/1995 | Burrell |
| 5,468,562 A | 11/1995 | Farivar |
| 5,520,664 A | 5/1996 | Bricault, Jr. |
| 5,622,711 A | 4/1997 | Chen |
| 5,633,010 A | 5/1997 | Chen |
| 5,681,575 A | 10/1997 | Burrell |
| 5,685,837 A | 11/1997 | Horstmann |
| 5,695,857 A | 12/1997 | Burrell et al. |
| 5,753,251 A | 5/1998 | Burrell |
| 5,888,594 A | 3/1999 | David |
| 6,861,570 B1 | 3/2005 | Flick |
| 6,994,904 B2 | 2/2006 | Joseph |
| 7,230,153 B2 | 6/2007 | Flick |
| 7,457,667 B2 | 11/2008 | Skiba |
| 8,224,439 B2 | 7/2012 | Skiba et al. |
| 8,460,568 B2 | 6/2013 | David |
| 8,634,146 B2 | 1/2014 | David |
| 2006/0204738 A1* | 9/2006 | Dubrow .................. A61L 27/34 428/292.1 |
| 2010/0150980 A1* | 6/2010 | Bokorny ................ A01N 59/16 424/421 |
| 2010/0318187 A1* | 12/2010 | Kruss ..................... B82Y 40/00 623/11.11 |
| 2011/0024159 A1* | 2/2011 | Allemand ................ C09D 7/70 174/126.1 |
| 2011/0313383 A1* | 12/2011 | Hofstetter ............... A61F 13/00 604/372 |
| 2012/0012557 A1* | 1/2012 | David ................. H01L 31/0236 216/71 |
| 2012/0181573 A1* | 7/2012 | Zaban ................... H01L 51/442 257/99 |
| 2013/0059984 A1* | 3/2013 | Kwon ................... B22F 1/0062 525/435 |
| 2013/0211310 A1* | 8/2013 | Bommarito ........... B08B 17/065 602/48 |
| 2015/0077854 A1 | 3/2015 | Yu et al. |

FOREIGN PATENT DOCUMENTS

| | | | |
|---|---|---|---|
| WO | WO-9841095 A2 * | 9/1998 | ....... A61F 13/00055 |
| WO | WO 2007/051996 A1 | 5/2007 | |
| WO | WO 2010-052190 | 5/2010 | |
| WO | WO 2010-056541 | 5/2010 | |
| WO | WO 2010-056543 | 5/2010 | |
| WO | WO 2010/139451 A2 | 12/2010 | |
| WO | WO 2012-058086 | 5/2012 | |
| WO | WO 2014/066850 A2 | 5/2014 | |
| WO | WO 2014-149718 | 9/2014 | |
| WO | WO 2015-013387 | 1/2015 | |

OTHER PUBLICATIONS

International Search Report for PCT International Application No. PCT/US2016/040136, dated Oct. 6, 2016, 4pgs.

* cited by examiner

ANTI-MICROBIAL ARTICLES AND METHODS OF USING SAME

BACKGROUND

The risk of being infected from medical devices is particularly high in the medical field. Anti-microbial articles or coatings are used extensively to prevent/reduce infections in the medical community. For example, medical devices used by doctors, including orthopedic pins, plates and implants, wound dressings, etc., must constantly guard against infection. Metallic ions with anti-microbial properties, such as Ag, Au, Pt, Pd, Ir, Cu, Sn, Sb, Bi and Zn, were used as anti-microbial compounds. Of these metallic ions, silver is known due to its good bioactivity. Various silver salts, complexes and colloids have been used to prevent and control infection.

SUMMARY

Although soluble salts of silver have been currently used to prevent microbial infections, they do not provide prolonged release of silver ions due to loss through removal or complexation of the free silver ions. They must be reapplied periodically to address this problem. Sometimes, reapplication is burdensome or sometimes even impractical, for example, when implanted medical devices are involved. Thus, it is desirable to have an anti-microbial article to provide a more effective release of anti-microbial agents.

In various exemplary embodiments described herein, the disclosed articles may be used to prevent microbial infections. The disclosed articles may be useful to provide an enhanced release of anti-microbial agents and thus to provide an increased anti-microbial activity.

In one aspect, the disclosure provides an article that includes an occlusive layer and a substrate having a nanostructured surface. The nanostructured surface is coated with a metal oxide layer and the metal oxide layer includes a metal oxide.

Some other aspects of the present disclosure provide a method of using the article. The method can include providing the article and applying the article to a subject, wherein the article exhibits a more than 4 log reduction of bacterial growth within 7 days.

Other features and aspects of the present disclosure will become apparent by consideration of the detailed description.

DEFINITIONS

Certain terms are used throughout the description and the claims that, while for the most part are well known, may require some explanation. It should be understood that, as used herein:

The terms "about" or "approximately" with reference to a numerical value or a shape means +/− five percent of the numerical value or property or characteristic, but also expressly includes any narrow range within the +/− five percent of the numerical value or property or characteristic as well as the exact numerical value. For example, a temperature of "about" 100° C. refers to a temperature from 95° C. to 105° C., but also expressly includes any narrower range of temperature or even a single temperature within that range, including, for example, a temperature of exactly 100° C.

The terms "a", "an", and "the" include plural referents unless the content clearly dictates otherwise. Thus, for example, reference to a material containing "a compound" includes a mixture of two or more compounds.

The term "or" is generally employed in its sense including "and/or" unless the content clearly dictates otherwise.

The term "molecular weight" as used throughout this specification means weight average molecular weight unless expressly noted otherwise.

The term "monomer" means a relatively low molecular weight material (i.e., having a molecular weight less than about 500 g/mole) having one or more radically polymerizable groups.

The term "oligomer" means a relatively intermediate molecular weight material having a molecular weight in a range from about 500 g/mole to about 10,000 g/mole.

The term "(co)polymer" means a relatively high molecular weight material having a molecular weight of at least about 10,000 g/mole (in some embodiments, in a range from 10,000 g/mole to 5,000,000 g/mole). The terms "(co)polymer" or "(co)polymers" includes homopolymers and copolymers, as well as homopolymers or copolymers that may be formed in a miscible blend, e.g., by co-extrusion or by reaction, including, e.g., transesterification. The term "(co)polymer" includes random, block and star (e.g. dendritic) (co)polymers.

The term "(meth)acrylate" with respect to a monomer, oligomer or means a vinyl-functional alkyl ester formed as the reaction product of an alcohol with an acrylic or a methacrylic acid.

The term "anisotropic" refers to a feature or structure having a height to width (that is, average width) ratio (aspect ratio) of about 1.5:1 or greater (preferably, 2:1 or greater; more preferably, 5:1 or greater);

The term "nanoscale" refers to features or structures having a characteristic length, width or height of no more than one micrometer (1,000 nanometers), for example, between about 1 nanometer (nm) and about 1,000 nm, more preferably between about 1 nm and 500 nm, most preferably between about 5 nm and 300 nm);

The term "nanostructure" or "nanostructured" refers to an article having at least one nanoscale feature or structure, and preferably a plurality of nanoscale features or structures; and The term "plasma" refers to a partially ionized gaseous or fluid state of matter containing electrons, ions, neutral molecules, and free radicals.

The term "fluoropolymer" refers to a homopolymer or a copolymer derived from interpolymerized units of at least one of the following monomers: tetrafluoroethylene (TFE), vinylidene fluoride (VDF), vinyl fluorine (VF), hexafluoropropylene (HFP), chlorotrifluoroethylene (CTFE), fluoroalkyl vinyl ethers, fluoroalkoxy vinyl ethers, fluorinated styrenes, hexafluoropropylene oxide (HFPO), fluorinated siloxanes, or combinations thereof.

The term "wetting time" refers to the time period between when a drop of colored water is added to the surface of an article and when the water drop is completely absorbed into the article.

The term "Water Contact Angle Measurement" refers the following measurement. Water contact angle was measured with a static contact angle measurement device. The machine is equipped with a digital camera, automatic liquid dispensers, and sample stages allowing hands-free contact angle via automated placement of a drop of water. The drop shape is captured automatically and then analyzed via Drop Shape Analysis by a computer to determine the static contact angle.

BRIEF DESCRIPTION OF THE DRAWINGS

The disclosure may be more completely understood in consideration of the following detailed description of vari

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. At the very least, and not as an attempt to limit the application of the doctrine of equivalents to the scope of the claimed embodiments, each numerical parameter should at least be construed in light of the number of reported significant digits and by applying ordinary rounding techniques. In addition, the use of numerical ranges with endpoints includes all numbers within that range (e.g. 1 to 5 includes 1, 1.5, 2, 2.75, 3, 3.80, 4, and 5) and any narrower range or single value within that range.

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

Figure 1:
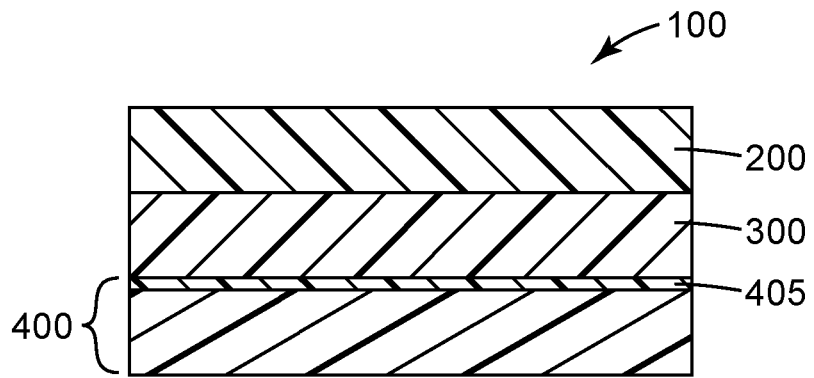
- FIG. 1 is a cross-sectional view of an exemplary anti-microbial article of the present disclosure.

An article is disclosed herein. FIG. 1 is a cross-sectional view of an exemplary anti-microbial article 100. Overall, article 100 includes an occlusive layer 200 and a substrate 400 overlaying the occlusive layer. Substrate 400 often has a nanostructured surface, which is provided with a nanostructure 405. The nanostructured surface of substrate 400 can be coated with a metal oxide layer 300. In the embodiment shown in FIG. 1, metal oxide layer 300 adjoins occlusive layer 200. Alternatively, substrate 400 can be next to the occlusive layer. An optional absorbent layer can be provided with occlusive layer 200.

If desired, an additional adhesive layer (not shown) can be supplied to substrate 400. In some embodiments, adhesive layer covers the entire surface of substrate 400. However, it is understood that the adhesive layer may cover only a portion of the surface of substrate 400. The article may include an optional release liner (not shown) that covers all or a portion of the adhesives to prevent contamination of the adhesives. An optional carrier (not shown) may be included to cover all or a portion of occlusive layer 200, providing structural support if the article is thin and highly flexible. The carrier may be removable from occlusive layer 200 once the article is placed on a subject.

Figure 2:
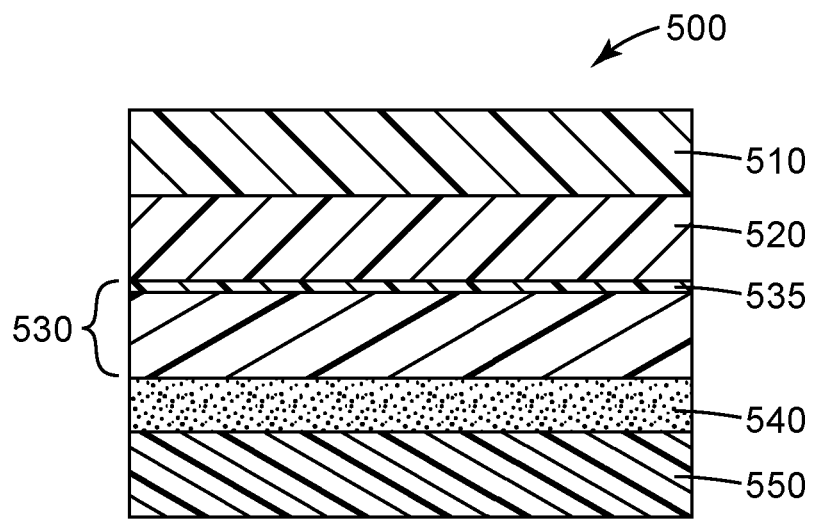
FIG. 2 is a cross-sectional view of an exemplary anti-microbial article of the present disclosure.
Figure 3:
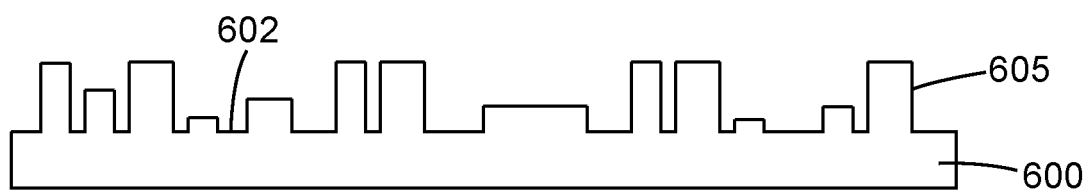
FIG. 3 is a schematic view of an exemplary substrate with a nanostructured surface.

FIG. 2 is a cross-sectional view of another exemplary anti-microbial article 500. Overall, article 500 includes an occlusive layer 550 and a substrate 530 overlaying the occlusive layer. Substrate 530 often has a nanostructure 405 on its nanostructured surface. The nanostructured surface of substrate 530 can be coated with a metal oxide layer 520. If desired, an additional adhesive layer 540 can be supplied to substrate 530 and occlusive layer 550. An optional release liner 510 can be supplied to metal oxide layer 520. The release liner 510 may be removed from metal oxide layer 520 before the article is placed on a subject. In the embodiment shown in FIG. 2, metal oxide layer 520 covers the entire surface of release liner 510 and substrate 530 covers the entire surface of adhesive layer 540. However, it is understood that the metal oxide layer may cover only a portion of the surface of release liner and substrate may cover only a portion of the surface of adhesive layer.

The article of the present disclosure can be used to provide an anti-microbial effect. The article can be provided to a health care provider and can be applied to a subject to release anti-microbial agents.

Occlusive Layer

The occlusive layers are useful to provide an impermeable barrier to the passage of liquids and at least some gases. Occlusive layers can be porous or non-porous. Representative barriers may include non-woven and woven fibrous webs, knits, films, foams, polymeric films and other familiar backing materials. In some embodiments, a transparent occlusive layer is desirable to allow for viewing of the underlying subjects. Suitable occlusive layers may include those described in International Publication No. WO 2014/149718, the disclosures of which are hereby incorporated by reference.

In one embodiment, the occlusive layer has high moisture vapor permeability, but generally impermeable to liquid water so that microbes and other contaminants are sealed out from the area under the article. One example of a suitable material is a high moisture vapor permeable film such as described in U.S. Pat. Nos. 3,645,835 and 4,595,001, the disclosures of which are herein incorporated by reference. In one embodiment, the occlusive layer can be an elastomeric polyurethane, polyester, or polyether block amide films. These films combine the desirable properties of resiliency, elasticity, high moisture vapor permeability, and transparency. A description of this characteristic of occlusive layers can be found in issued U.S. Pat. Nos. 5,088,483 and 5,160,315, the disclosures of which are hereby incorporated by reference Commercially available examples of potentially suitable materials for the occlusive layer may include the thin polymeric film sold under the trade names TEGADERM (3M Company), OPSITE (Smith & Nephew), etc. Because fluids may be actively removed from the sealed environments defined by the article, a relatively high moisture vapor permeable occlusive layer may not be required. As a result, some other potentially useful materials for the occlusive layer may include, e.g., metallocene polyolefins and SBS and SIS block copolymer materials.

Regardless, however, it may be desirable that the occlusive layer be kept relatively thin to, e.g., improve conformability. For example, the occlusive layer may be formed of polymeric films with a thickness of 200 micrometers or less, or 100 micrometers or less, 50 micrometers or less, or 25 micrometers or less.

Substrate with a Nanostructured Surface

FIG. 2 is a schematic view of an exemplary substrate with a nanostructured surface. The nanostructured surface 602 of substrate 600 typically can comprise nanostructures (nanoscale features) 605 of diverse height and aspect ratio. Generally, the nanostructured surface can have a nanostructured anisotropic surface. The nanostructured anisotropic surface typically can comprise nanoscale features. In some embodiments, the nanostructured anisotropic surface can comprise anisotropic nanoscale features. In some embodiments, the nanostructured anisotropic surface can comprise random anisotropic nanoscale features. The nanostructured anisotropic surface typically can comprise nanoscale features having a height to width ratio (aspect ratio) about 2:1 or greater; preferably about 5:1 or greater. In some embodiments, the height to width ratio can even be 50:1 or greater, 100:1 or greater, or 200:1 or greater. The nanostructured anisotropic surface can comprise nanoscale features such as, for example, nano-pillars or nano-columns, or continuous nano-walls comprising nano-pillars or nano-columns. Typically, the nanoscale features have steep side walls that are substantially perpendicular to the substrate.

The substrate with the nanostructured surface can be formed by any suitable means, including plasma treatment process. Suitable process can include those described in U.S. Pat. Nos. 5,888,594, 8,460,568, 8,634,146 and International Publication No. WO 2015/013387, the disclosures of which are hereby incorporated by reference.

The substrate can be made of any material that can be etched by the methods disclosed in U.S. Pat. Nos. 5,888,594, 8,460,568, 8,634,146 and International Publication No. WO 2015/013387. For example, the substrate can be a (co)polymeric material, an inorganic material, an alloy, or a solid solution. In some embodiments, the substrate can include a fiber, a glass, a composite, or a microporous membrane.

(Co)polymeric materials include thermoplastics and thermosetting plastics. Typical thermoplastics include, but are not limited to, polyethylene terephthalate (PET), polystyrene, acrylonitrile butadiene styrene, polyvinyl chloride, polyvinylidene chloride, polycarbonate, polyacrylates, thermoplastic polyurethanes, polyvinyl acetate, polyamide, polyimide, polypropylene, polyester, polyethylene, poly(methylmethacrylate), polyethylene naphthalate, polystyrene acrylonitrile, triacetate cellulose, nylon, silicone-polyoxamide polymers, fluoropolymers, cyclic olefin copolymers, and thermoplastic elastomers. Suitable thermosets include, but are not limited to, allyl resins, epoxies, thermosetting polyurethanes, and silicones or polysiloxanes. These resins can be formed from the reaction product of polymerizable compositions comprising at least one oligomeric urethane (meth)acrylate. Typically, the oligomeric urethane (meth)acrylate is a multi(meth)acrylate. The term "(meth)acrylate" is used to designate esters of acrylic and methacrylic acids, and "multi(meth)acrylate" designates a molecule containing more than one (meth)acrylate group, as opposed to "poly(meth)acrylate" which commonly designates (meth)acrylate polymers. Most often, the multi(meth)acrylate is a di(meth)acrylate, but it is also contemplated to employ tri(meth)acrylates, tetra(meth)acrylates and so on.

Oligomeric urethane multi(meth)acrylates may be obtained commercially, for example from Sartomer under the trade designation "PHOTOMER 6000 Series", such as "PHOTOMER 6010" and "PHOTOMER 6020", and also under the trade designation "CN 900 Series", such as "CN966B85", "CN964" and "CN972". Oligomeric urethane (meth)acrylates are also available from Surface Specialties, such as available under the trade designations "EBECRYL 8402", "EBECRYL 8807" and "EBECRYL 4827". Oligomeric urethane (meth)acrylates may also be prepared by the initial reaction of an alkylene or aromatic diisocyanate of the formula OCN—$R_3$—NCO with a polyol.

Most often, the polyol is a diol of the formula HO—$R_4$—OH wherein $R_3$ is a $C_{2-100}$ alkylene or an arylene group and $R_4$ is a $C_{2-100}$ alkylene group. The intermediate product is then a urethane diol diisocyanate, which subsequently can undergo reaction with a hydroxyalkyl (meth)acrylate. Suitable diisocyanates include 2,2,4-trimethylhexylene diisocyanate and toluene diisocyanate. Alkylene diisocyanates are generally useful. A compound of this type may be prepared from 2,2,4-trimethylhexylene diisocyanate, poly(caprolactone)diol and 2-hydroxyethyl methacrylate. In at least some cases, the urethane (meth)acrylate can be aliphatic. Also included can be (meth)acrylate esters having other functionality. Compounds of this type are exemplified by the 2-(N-butylcarbamyl)ethyl (meth)acrylates, 2,4-dichlorophenyl acrylate, 2,4,6-tribromophenyl acrylate, tribromophenoxylethyl acrylate, t-butylphenyl acrylate, phenyl acrylate, phenyl thioacrylate, phenylthioethyl acrylate, alkoxylated phenyl acrylate, isobornyl acrylate and phenoxyethyl acrylate. The reaction product of tetrabromobisphenol A diepoxide and (meth)acrylic acid is also suitable.

The other monomer may also be a monomeric N-substituted or N,N-disubstituted (meth)acrylamide, especially an acrylamide. These include N-alkylacrylamides and N,N-dialkylacrylamides, especially those containing $C_{1-4}$ alkyl groups. Examples are N-isopropylacrylamide, N-t-butylacrylamide, N,N-dimethylacrylamide and N,N-diethylacrylamide.

The other monomer may further be a polyol multi(meth)acrylate. Such compounds are typically prepared from aliphatic diols, triols, and/or tetraols containing 2-10 carbon atoms. Examples of suitable poly(meth)acrylates are ethylene glycol diacrylate, 1,6-hexanediol diacrylate, 2-ethyl-2-hydroxymethyl-1,3-propanediol triacylate (trimethylolpropane triacrylate), di(trimethylolpropane) tetraacrylate, pentaerythritol tetraacrylate, the corresponding methacrylates and the (meth)acrylates of alkoxylated (usually ethoxylated) derivatives of said polyols.

Monomers having two or more ethylenically unsaturated groups can serve as a crosslinker. Styrenic compounds suitable for use as the other monomer include styrene, dichlorostyrene, 2,4,6-trichlorostyrene, 2,4,6-tribromostyrene, 4-methylstyrene and 4-phenoxystyrene. Ethylenically unsaturated nitrogen heterocycles include N-vinylpyrrolidone and vinylpyridine.

Useful inorganic materials for the substrate include, for example, glasses, metals, metal oxides, and ceramics. In some embodiments, inorganic materials include silicon, silicon oxide, germanium, zirconia, vanadium pentoxide, molybdenum, copper, titanium, titanium dioxide, gallium arsenide, diamond, aluminum oxide, silicon nitride, indium tin oxide, and tungsten carbide.

The substrate having the nanostructured surface can exhibit one or more desirable properties such as antireflective properties, light absorbing properties, antifogging properties, improved adhesion and durability. For example, in some embodiments, the nanostructured anisotropic surface can have a water contact angle of less than about 20°, less than about 15°, or even less than about 10° as measured using the "Water Contact Angle Measurement" method described in the Definition section above.

Metal Oxide Layer

The metal oxide layer of the present disclosure includes a metal oxide. The metal oxide can be those known to have an anti-microbial effect. For most medical use, the metal oxide can also be biocompatible. In some embodiments, the metal oxide used in the metal oxide layer can include, but is not limited to, silver oxide, copper oxide, gold oxide, zinc oxide, magnesium oxide, titanium oxide, chromium oxide and combinations thereof. In some of these embodiments, the metal oxide can be silver oxide, including but not limited to, $Ag_2O$. In some embodiments, the metal oxide layer can include less than 99 wt. %, less than 95 wt. %, less than 90 wt. %, less than 80 wt. %, less than 40 wt. %, less than 20 wt. %, less than 10 wt. %, less than 5 wt. %, less than 1 wt. % non-oxidized metal. When the metal oxide layer includes more than 40 wt. % non-oxidized metal, the article will become more conductive, i.e., the resistivity of the article decreases, and the release of anti-microbial agents also decreases.

The metal oxide layer can be formed by any suitable means, for example, by physical vapor deposition techniques. The physical vapor deposition techniques can include, but is not limited to, vacuum or arc evaporation, sputtering, magnetron sputtering and ion plating. Suitable physical vapor deposition techniques can include those described in U.S. Pat. Nos. 4,364,995; 5,681,575 and 5,753,251, the disclosures of which are hereby incorporated by reference.

By the controlled introduction of reactive material, for example, oxygen into the metal vapor stream of vapor deposition apparatus during the vapor deposition of metals onto substrates, controlled conversion of the metal to metal oxides can be achieved. Therefore, by controlling the amount of the reactive vapor or gas introduced, the proportion of metal to metal oxide in the metal oxide layer can be controlled. For 100% conversion of the metal to metal oxides at a given level of the layer, at least a stoichiometric amount of the oxygen containing gas or vapor is introduced to a portion of the metal vapor stream. When the amount of the oxygen containing gas increases, the metal oxide layer will contain a higher weight percent of metal oxide. The ability to achieve release of metal atoms, ions, molecules or clusters on a sustainable basis can be effected by varying the amount of the oxygen containing gas. As the amount of metal oxide increases when the level of oxygen containing gas introduced increases, metal ions released from the article in turn increases. Thus, a higher weight percent of metal oxide can, for example, provide an enhanced release of anti-microbial agents, such as metal ions and provide an increased anti-microbial activity.

The metal oxide layer can be formed as a thin film. The film can have a thickness no greater than that needed to provide release of metal ions on a sustainable basis over a suitable period of time. In that respect, the thickness will vary with the particular metal in the coating (which varies the solubility and abrasion resistance), and with the amount of the oxygen containing gas or vapor introduced to the metal vapor stream. The thickness will be thin enough that the metal oxide layer does not interfere with the dimensional tolerances or flexibility of the article for its intended utility. Typically, the metal oxide layer has a thicknesses of less than 1 micron. However, it is understood that increased thicknesses may be used depending on the degree of metal ion release needed over a period of time.

Optional Components

The absorbent materials used in the absorbent layer can be manufactured from any suitable materials including, but not limited to, woven or nonwoven cotton or rayon. An absorbent pad can be used as the absorbent layer and can be useful for containing a number of substances, optionally including drugs for transdermal drug delivery, chemical indicators to monitor hormones or other substances in a patient, etc.

The absorbent layer may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. The absorbent layer can be manufactured of other synthetic and natural hydrophilic materials including polymer gels and foams.

Suitable adhesive for use in the article includes any adhesive that provides acceptable adhesion to skin and is acceptable for use on skin (e.g., the adhesive should preferably be non-irritating and non-sensitizing). Suitable adhesives are pressure sensitive and in certain embodiments have a relatively high moisture vapor transmission rate to allow for moisture evaporation. Suitable pressure sensitive adhesives include those based on acrylates, urethane, hyrdogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent. Suitable adhesive can include those described in U.S. Pat. Nos. 3,389,827; 4,112,213; 4,310,509; 4,323,557; 4,595,001; 4,737,410; 6,994,904 and International Publication Nos. WO 2010/056541; WO 2010/056543 and WO 2014/149718, the disclosures of which are hereby incorporated by reference.

Suitable release liners can be made of kraft papers, polyethylene, polypropylene, polyester or composites of any of these materials. In one embodiment, the package that contains the adhesive dressing may serve as a release liner. In one embodiment, the liners are coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials.

The carrier used in the article can be constructed of any suitable materials such as fabric that are woven or knitted, nonwoven material, papers, or film. In one embodiment, the carrier is along the perimeter of the occlusive layer and is removable from the occlusive layer, similar to the carrier used the 3M Tegaderm Transparent Film Dressing, available from 3M Company, St. Paul, Minn.

Properties

The anti-microbial effect of the article can be achieved, for example, when the article is brought into contact with an alcohol or a water based electrolyte such as, a body fluid or body tissue, thus releasing metal ions such as $Ag^+$, atoms, molecules or clusters. The concentration of the metal which is needed to produce an anti-microbial effect will vary from metal to metal. Generally, anti-microbial effect is achieved in body fluids such as plasma, serum or urine at concentrations less than 10 ppm. In some embodiments, $Ag^+$ release concentration from the article can be 0.1 ppm, 0.5 ppm, 1 ppm, 2 ppm, 2.5 ppm, 3 ppm, 4 ppm, 5 ppm, 6 ppm, 7 ppm, 8 ppm, 9 ppm, 10 ppm or a range between and including any two of these values. As discussed above, when the amount of metal oxide in the metal oxide layer increases, the metal ions released from the article in turn increases. For example, a more than 60 wt. % metal oxide provides an enhanced release of metal ions from the article. Therefore, the article of the present disclosure can provide a very effective antimicrobial effect. In some embodiments, the article can exhibit a more than 4 log reduction of bacterial growth within 7 days. In some embodiments, the article can exhibit a more than 6 log reduction of bacterial growth within 7 days.

In some embodiments, the article of the present disclosure can have a more than 50%, more than 100%, more than 150%, more than 200%, more than 300%, more than 400%, more than 500%, or more than 600% absorbency. Absorbency of the article generally relates to the capacity of absorbing wound fluid (exudate), when the article is used as a medical dressing. Articles with a high absorbency can absorb more exudate. This can, for example, help decrease the risk of maceration and irritation to the wound and surrounding tissues and the frequency of replacing the articles. In some embodiments, the article of the present disclosure can have a less than 3 minutes, less than 2 minutes, or less than 1 minute wetting time. Wetting time of the article generally relates to the absorption rate of fluid into the article. Shorter wetting time can enhance the overall fluid management profile, for example, increasing the timer interval between replacing the articles. At the early stage of healing a wound, the article with a shorter wetting time can quickly remove fluid, which in turns minimizes the potential risk of infection.

Various exemplary embodiments of the present disclosure are further illustrated by the following listing of embodiments, which should not be construed to unduly limit the present disclosure:

EMBODIMENTS

1. An article comprising:
   an occlusive layer; and
   a substrate having a nanostructured surface;
   wherein the nanostructured surface is coated with a metal oxide layer;
   wherein the metal oxide layer comprises a metal oxide.
2. The article of embodiment 1, wherein the metal oxide layer comprises less than 99 wt. % non-oxidized metal.
3. The article of embodiment 2, wherein the metal oxide layer comprises less than 95 wt. % non-oxidized metal.
4. The article of embodiment 3, wherein the metal oxide layer comprises less than 80 wt. % non-oxidized metal.
5. The article of embodiment 4, wherein the metal oxide layer comprises less than 40 wt. % non-oxidized metal.
6. The article of embodiment 5, wherein the metal oxide layer comprises less than 20 wt. % non-oxidized metal.
7. The article of embodiment 6, wherein the metal oxide layer comprises less than 10 wt. % non-oxidized metal.
8. The article of embodiment 7, wherein the metal oxide layer comprises less than 5 wt. % non-oxidized metal.
9. The article of embodiment 8, wherein the metal oxide layer comprises less than 1 wt. % non-oxidized metal.
10. The article of embodiment 1, wherein the nanostructured surface comprises an anisotropic nanostructure.
11. The article of embodiment 10, wherein the anisotropic nanostructure has an aspect ratio greater than 2:1.
12. The article of any of embodiments 1 to 11, wherein the metal oxide is selected from silver oxide, copper oxide, gold oxide, zinc oxide, magnesium oxide, titanium oxide, chromium oxide and combinations thereof.
13. The article of embodiment 12, wherein the metal oxide is silver oxide.
14. The article of embodiment 13, wherein the silver oxide is $Ag_2O$.
15. The article of embodiment 14, wherein $Ag^+$ release concentration of the article is more than 3.5 ppm.
16. The article of embodiment 15, wherein $Ag^+$ release concentration of the article is more than 5 ppm.
17. The article of any of embodiment 16, wherein $Ag^+$ release concentration of the article is more than 8 ppm.
18. The article of any of embodiments 1 to 17, wherein the metal oxide layer is formed by physical vapor deposition.
19. The article of any of embodiments 1 to 18, further comprising an adhesive layer overlaying the substrate.
20. The article of any of embodiments 1 to 19, further comprising release liners overlaying the metal oxide layer.
21. The article of any of embodiments 1 to 20, wherein the article exhibits a more than 4 log reduction of bacterial growth within 7 days.
22. The article of any of embodiments 1 to 21, wherein the article exhibits a more than 6 log reduction of bacterial growth within 7 days.
23. The article of any of embodiments 1 to 22, wherein wetting time of the article is less than 3 minutes.
24. The article of any of embodiments 1 to 23, wherein wetting time of the article is less than 2 minutes.
25. The article of any of embodiments 1 to 24, wherein absorbency of the article is more than 50%.
26. A method of use of the article of embodiment 1, comprising the steps of:
    providing the article of embodiment 1; and
    applying the article to a subject;
    wherein the article exhibits a more than 4 log reduction of bacterial growth within 7 days.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Unless otherwise noted, all parts, percentages, ratios, etc. in the Examples and the rest of the specification are provided on the basis of weight. Solvents and other reagents used may be obtained from Sigma-Aldrich Chemical Company (Milwaukee, Wis.) unless otherwise noted.

The provided articles described herein were prepared via sputtering deposition. Silver films were coated onto 152 mm by 152 mm substrates by magnetron physical vapor deposition. The films were sputtered from a 76.2 mm round silver target in a batch coater. The substrate was placed on a substrate holder set up inside a vacuum chamber with a sputtering metal target located at a height of 228.6 mm above the substrate holder. After the chamber was evacuated to 2×10-5 torr base pressure, sputter gases of argon and reactive oxygen were admitted inside the chamber and total pressure of the chamber was adjusted to either 5 millitorr or 20 millitorr. Sputtering was initiated using a DC power supply at a constant power level of 0.25 kilowatts. The sputtering duration was varied to produce a same coating weight per unit area of 0.05 mg/cm$^2$.

Nanostructure Pretreatment Process

The nanostructures were obtained by essentially using a homebuilt plasma treatment system described in U.S. Pat. No. 5,888,594 and International Publication No. WO 2015/013387. The width of the drum electrode was increased to 42.5 inches (108 cm) and the separation between the two compartments within the plasma system was removed so that all the pumping was carried out by means of the turbo-molecular pump and thus operating at a much lower operating pressure than is conventionally done with plasma processing. Rolls of polymeric substrate were mounted within the chamber, the substrate wrapped around the drum electrode and secured to the take up roll on the opposite side of the drum. The unwind and take-up tensions were maintained at 3 pounds (13.3N). The chamber door was closed and the chamber pumped down to a base pressure of 0.5 millitorr. Gases such as oxygen and hexamethyldisiloxane (HMDSO) were then introduced into the chamber. The operating pressure was nominally 5 millitorr or 10 millitorr. Plasma was generated by applying a power of 6000 watts of radio frequency energy to the drum. The drum was rotated so that the film was transported at a desired speed for the specific treatment time as stated in the specific example. For a piece-part substrate, the sample was either attached to a web carrier or to the surface of drum electrode to be treated at a desired speed for the specific etching time as stated in the specific example.

Measurement of Light Transmission

Measurement of transmission was carried out with BYK Haze-Gard Plus (from BYK Gardiner, Columbia, Md.) according to ASTM D1003 & D1004.

Measurement of Surface Resistivity

The surface resistivity was measured using a Fluke 175 True RMS Multimeter or contact-less resistance meter, Delcom model 717B conductance monitor.

Measurement of Ag$^+$ Release

The electrode (Orion Sure-flow IonPlus Silver/Sulfide combination ion selective electrode, model 9616BN) slope was checked. Ag$^+$ standard solutions were prepared. The electrode was calibrated daily by immersion in 0.3, 1, 10, and 100 ppm Ag$^+$ standard solutions. The silver ion release of the article was evaluated as follows. 60 mL of water, 1 mL ISA, and 50 μL of the 1000 ppm silver standard solution were added to a 100 mL disposable beaker and a stir bar was added. The initial potential on the Ag ISE was recorded. 3 cm$^2$ of the article was added to the beaker and the timer started. Free silver ion concentration in solution was recorded at ten second intervals by the Tiamo 2.4 software (from Metrohm, Herisau, Switzerland) for 60 minutes.

Log Reduction Testing

The modified JIS Z 2801 test method (Japan Industrial Standards; Japanese Standards Association; Tokyo, JP) was used to evaluate the antibacterial activity of the articles. The bacterial inoculum was prepared in a solution of 1 part Nutrient Broth (NB) and 499 parts phosphate buffer. A portion of the bacterial suspension (150 μl) was placed onto the surface of the article and the inoculated article was incubated for the specified contact time at 27+/−1° C. After incubation, the article was placed into 20 ml of D/E Neutralizing Broth. The number of surviving bacteria in the Neutralizing broth was determined by using 3M Petrifilm (3M, St. Paul, Minn.).

Zone of Inhibition Test

Zone of inhibition test (Kirby-Bauer disk diffusion susceptibility test) was used to determine the sensitivity or resistance of bacteria to antimicrobial leaching compounds of the articles. The microorganism is grown on Mueller-Hinton agar in the presence of antimicrobial impregnated into disks of material. The presence or absence of zone around the disks is an indirect measure of the ability of that compound to inhibit that organism.

Absorbency Test

A silver coated absorbent article was weighed [W(0)] and then soaked in water for T hour. The article was removed from the water at specified time (T) and reweighed [W(T)]. The weight of water absorbed [W(T)-W(0)] was divided by the initial weight of the absorbent article [W(0)] to calculate absorbency, which was reported as % absorption at specified time.

Substrate Wetting Time (Time to Complete Immersion) Test

Wetting time was measured by adding a drop of colored water to silver coated absorbent article and recording the time when the water drop was completely absorbed into the article.

Example 1 & Comparative 1

400 gm of 75 nm silica particles (obtained from Nalco Chemical Co., under the trade designation "NALCO 2329K") was charged into a 1 quart (0.95 liter) jar. Four hundred fifty grams of 1-methoxy-2-propanol, 9.2 grams of 3-(Methacryloyloxy)propyltrimethoxy silane, and 0.23 gram of hindered amine nitroxide inhibitor (obtained from BASF Specialty Chemicals, under the trade designation "PROSTAB 5128") in water at 5 wt. % inhibitor were mixed together and added to the jar while stirring. The jar was sealed and heated to 80° C. for 16 hours to form a surface-modified silica dispersion. The water was further removed from the mixture via rotary evaporation to form a solution of 42.4 percent by weight 75 nm SiO2 in 1-methoxy-2-propanol.

7.1 gm of the 42.4 percent functionalized 75 nm SiO2 solution, 12 gm of trimethylolpropantriacrylate (TMPTA) from Sartomer, under the trade designation "SR351", 31 gm of isopropanol and 0.15 gm of IGARCURE 184 from BASF Specialty Chemicals were blended and mixed to form a coating solution. The coating was applied on 5 mil PET using a Mayer rod (#4 bar) coating device.

The coated substrate was dried at room temperature inside a ventilated hood for 5 minutes and then cured using a UV processor equipped with a H-Bulb under a nitrogen atmosphere at 50 fpm (15.24 meter/minute). The cured coated substrate was then subjected to the O2 plasma nanostructure treatment described above for a treatment time of 180 seconds at 5 millitorr.

The coated substrates with and without the O2 plasma etching treatment were further coated with silver by sputtering deposition process described above using sputter gases of 6.3% O2 by flow rate at 20 millitorr. The Ag ion release results are displayed in Table 2.

TABLE 1

Ag + release for Example 1 and Comparative 1

| | | % O2 | Ag+ release concentration (ppm) |
|---|---|---|---|
| Example 1 | coated PET with O2 plasma etching pre-treatment | 6.3 | 8.1 |
| Comparative 1 | coated PET without O2 plasma etching pre-treatment | 6.3 | 2.5 |

Example 2 and Comparative 2

Polypropylene fabrics were obtained from Midwest Filtration Co, under the trade designation UNIPRO 150 SMS and pretreated with the nanostructure treatment described above. The first gaseous species was hexamethyldisiloxane (HMDSO) vapor provided at a flow rate of 20 sccm, and the second gaseous species was oxygen provided at a flow rate of 500 sccm. The pressure during the exposure was around 10 millitorr and plasma was turned on at a power of 6000 watts. The treatment time was about 54 seconds. The polypropylene fabrics with and without nanostructure treatment were then coated with silver by sputtering deposition using a gas mixture of 6.8% O2 at 20 millitorr. Their Ag+ release and log growth testing results are provided in Table 3.

TABLE 2

Ag + release and log growth testing results for Example 2 and Comparative 2

| | | % O2 | Ag + release concentration (ppm) | S. aureus ATCC6538 Log Reduction CFU/cm2 (24 hours) |
|---|---|---|---|---|
| Example 2 | coated PP fabrics with plasma etching pre-treatment | 6.8 | 5.4 | 5.29 |
| Comparative 2 | coated PP fabrics without plasma etching pre-treatment | 6.8 | 3.5 | 3.43 |

Example 3

3M urethane Aero foam was pretreated by the plasma treatment in Example 2 and further coated with Ag by sputtering deposition using a gas mixture of 29% O2 at 20 millitorr. The coated sample was tested by log reduction testing and achieved >4.5 log reduction at the testing time of 2 hours and sustained its killing efficacy of >4.5 log reduction to 7 days. The absorbency of the coated sample is greater than 500%.

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An article comprising:
    an occlusive layer; and
    a substrate having a nanostructured surface, wherein the nanostructured surface comprises random anisotropic nanostructures;
    wherein nanostructures are formed from the substrate to produce the nanostructured surface;
    wherein the nanostructured surface is coated with a metal oxide layer;
    wherein the metal oxide layer comprises a metal oxide;
    wherein the metal oxide layer comprises less than 40 wt.% non-oxidized metal.

2. The article of claim 1, wherein the metal oxide is selected from silver oxide, copper oxide, gold oxide, zinc oxide, magnesium oxide, titanium oxide, chromium oxide and combinations thereof.

3. The article of claim 2, wherein the metal oxide is silver oxide.

4. The article of claim 3, wherein the silver oxide is $Ag_2O$.

5. The article of claim 4, wherein $Ag^+$ release concentration of the article is more than 3.5 ppm.

6. The article of claim 5, wherein $Ag^+$ release concentration of the article is more than 5 ppm.

7. The article of claim 6, wherein $Ag^+$ release concentration of the article is more than 8 ppm.

8. The article of claim 1, wherein the anisotropic nanostructure has an aspect ratio greater than 2:1.

9. The article of claim 1, wherein the metal oxide layer is formed by physical vapor deposition.

10. The article of claim 1, wherein the article exhibits a more than 4 log reduction of bacterial growth within 7 days.

11. The article of claim 1, wherein the article exhibits a more than 6 log reduction of bacterial growth within 7 days.

12. A method of use of the article of claim 1, comprising the steps of:
    providing the article of claim 1; and
    applying the article to a subject;
    wherein the article exhibits a more than 4 log reduction of bacterial growth within 7 days.

* * * * *